US 6,477,419 B2
Nov. 5, 2002

(54) IMPLANTABLE CARDIAC DEVICE PROVIDING REPETITIVE NON-REENTRANT VENTRICULO-ATRIAL SYNCHRONOUS (RNRVAS) RHYTHM THERAPY USING SECONDARY PACING PULSES AND METHOD

(75) Inventors: Paul A. Levine, Santa Clarita, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 76 days.

(21) Appl. No.: 09/795,409

(22) Filed: Feb. 27, 2001

(65) Prior Publication Data

US 2002/0120301 A1 Aug. 29, 2002

(51) Int. Cl.[7] .............................................. A61N 1/362
(52) U.S. Cl. ............................................. 607/14; 607/9
(58) Field of Search ................................ 607/9, 17, 25

(56) References Cited

U.S. PATENT DOCUMENTS 5,228,438 A * 7/1993 Buchanan ..................... 607/18
6,377,852 B1 * 4/2002 Bornzin et al. ................ 607/9

OTHER PUBLICATIONS

Barold, S. Serge, et al., Pacemaker Repetitive Nonreentrant Ventriculoatrial Synchronous Rhythm. A Review, Journal of Interventional Cardiac Electrophysiology, vol. 5, No. 1, pp 45–58, (Mar. 2001).

Levine, Paul A. et al; "Prospective Management of the Patient with Retrograde Ventriculoatrial Conduction; Prevention and Management of Pacemaker Mediated Endless Loop Tachycardias"; Pacesetter® Systems, Inc., pp 1–15; (Aug. 1990).

van Gelder, L.M. et al; "Ventriculoatrial Conduction: A Cause of Atrial Malpacing in AV Universal Pacemakers. A Report of Two Cases"; PACE; vol. 8; pp–140–143; (Jan.–Feb. 1985).

Levine, Paul A.; "Postventricular Atrial Refractory Periods and Pacemaker Mediated Tachycardias"; Clin. Prog. in Pacing and Electrophysiol; vol. 1, No. 4; pp 394–401; (1983).

\* cited by examiner

*Primary Examiner*—Carl Layno

(57) ABSTRACT

A system and method detects and terminates a repetitive nonreentrant ventriculo-atrial synchronous (RNRVAS) rhythm. The system and method is particularly adapted for use in an implantable cardiac stimulation device that includes a pulse generator that delivers atrial and ventricular pacing stimulation pulses and implements an atrial escape interval and a VA delay interval. This system includes a sensing circuit that senses cardiac activity of a heart and a detector that is responsive to the sensing circuit that determines if an RNRVAS rhythm is present. If an RNRVAS rhythm is present, a therapy control circuit causes the pulse generator to deliver a secondary atrial pacing pulse following a primary atrial pacing pulse delivered at the end of an atrial escape interval. The therapy control circuit may additionally cause the pulse generator to deliver a tertiary atrial pacing pulse following the next ventricular pacing pulse to prevent the occurrence of a retrograde P wave.

46 Claims, 6 Drawing Sheets

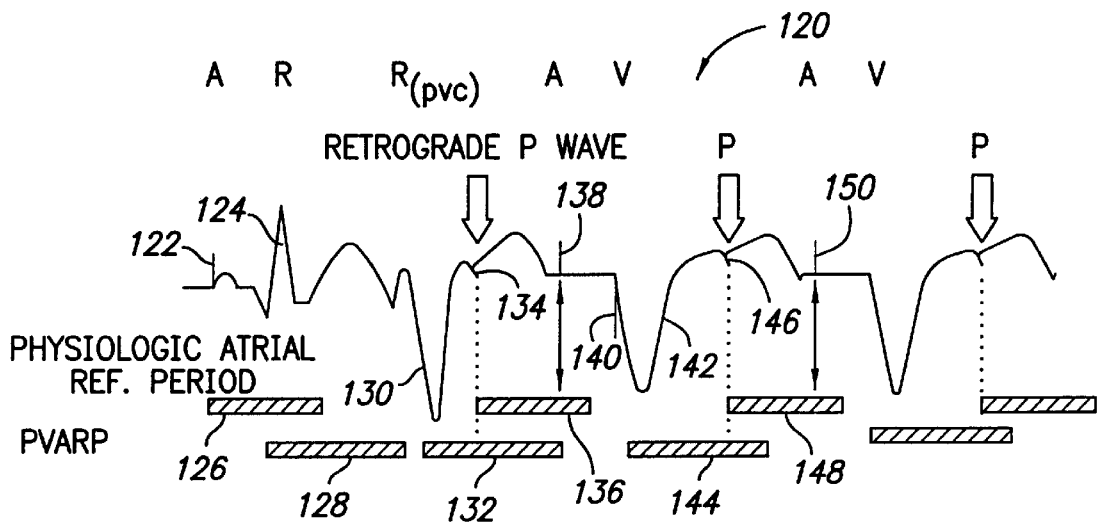
FIG. 3
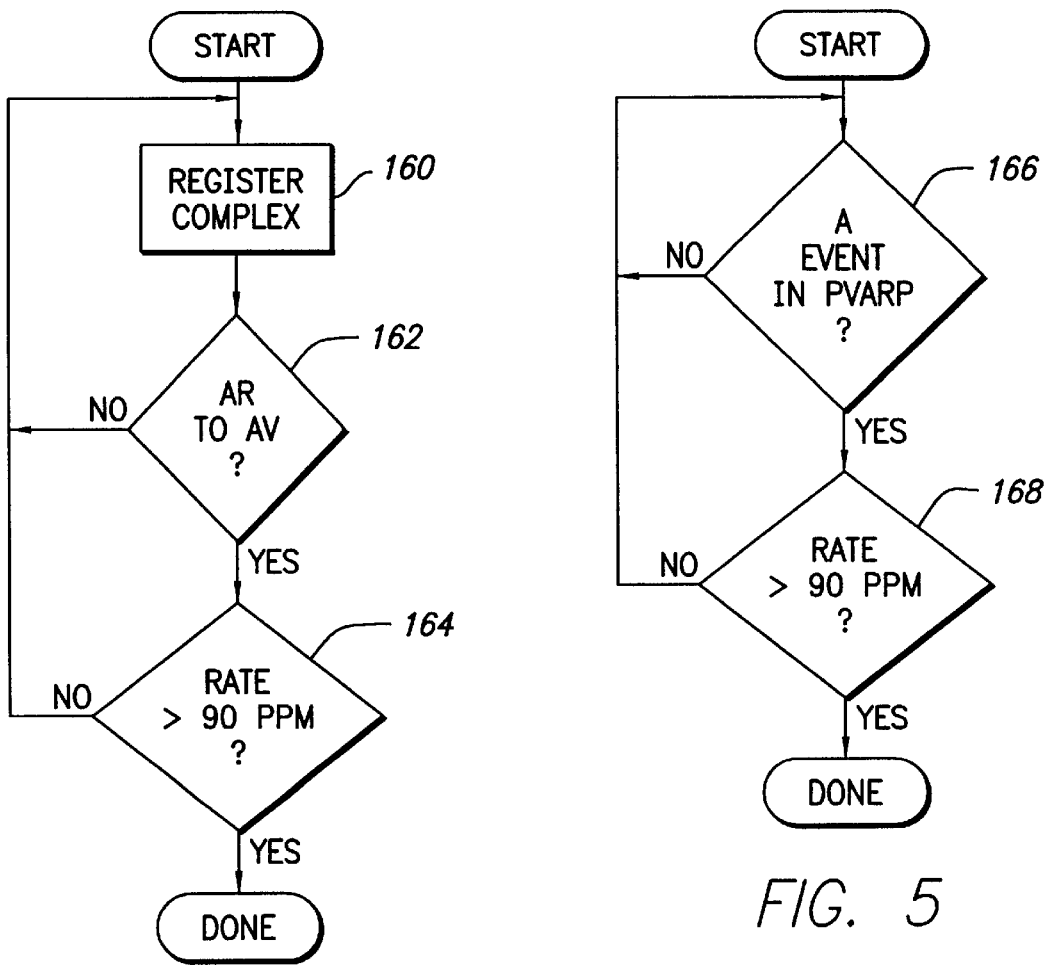
FIG. 4
FIG. 5

IMPLANTABLE CARDIAC DEVICE PROVIDING REPETITIVE NON-REENTRANT VENTRICULO-ATRIAL SYNCHRONOUS (RNRVAS) RHYTHM THERAPY USING SECONDARY PACING PULSES AND METHOD

FIELD OF THE INVENTION

The present invention generally relates to an implantable cardiac device. The present invention more particularly relates to an implantable pacemaker capable of detecting and providing therapy for repetitive non-reentrant ventriculo-atrial synchronous (RNRVAS) rhythms.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

A popular mode of operation for dual-chamber pacemakers is the DDD mode. Specifically, DDD systems provide atrial pacing during atrial bradycardia, ventricle pacing during ventricular bradycardia, and atrial and ventricular pacing during combined atrial and ventricular bradycardia or heart block also known as AV block. In addition, DDD systems provide an atrial synchronous mode. This enables ventricular activity to track atrial activity to more closely approximate the normal response to exercise, or other physiological activity demanding a faster heart rate, by permitting a rate increase to occur commensurate with the rate of the sensed P waves. This advantageously increases cardiac output and facilitates maintenance of AV synchrony.

Many dual-chamber pacemakers further incorporate a physiologic sensor. Such sensors are employed to detect the patient's degree of activity for regulating the heart rate. Hence, as the patient becomes more active, requiring increased cardiac output, the stimulation rate of the pacemaker is increased. When the patient becomes less active, requiring reduced cardiac output, the stimulation rate of the pacemaker is in turn decreased.

Dual-chamber pacemakers implement two main timing intervals to support their operation. These intervals are referred to as the AV delay interval and the VA interval, also referred to as the atrial escape interval. The AV delay interval is the time from an atrial pacing pulse or a detected P wave, if atrial activity is sensed, to when the next ventricular pacing pulse is to be delivered in the absence of a preoccurring R wave. Such pacing is referred to as atrial synchronous ventricular tracking and atrioventricular sequential pacing.

Similarly, the VA interval or atrial escape interval is the time from a detected R wave or a ventricular pacing pulse to when a next atrial pacing pulse is to be delivered absent a preoccurring P wave. This pacing is referred to as atrial demand pacing.

One condition that may occur during atrial synchronous pacing is a pacemaker mediated tachycardia (PMT). A PMT can result when the atrial sensing circuit detects a retrograde P wave (a P wave induced by a ventricular pacing pulse retrogradedly conducted from the ventricles back to the atria). When this occurs, the pacemaker initiates an AV delay interval and subsequently provides a ventricular pacing pulse at the end of the AV delay interval or the maximum tracking rate interval, which ever ends later. Repeated cycles of this stimulation pattern are sustained by the heart tissue retrograde conduction and by the pacemaker anterograde conduction.

Methods for preventing PMT are well known in the art. One such known method involves the use of a post ventricular atrial refractory period (PVARP) initiated by a ventricular pacing pulse or the detection of an intrinsic ventricular event which prohibits the atrial sensing circuit from sensing the retrograde P wave. The length of the PVARP is generally selected to be longer than the retrograde response time and may be divided into a first or absolute refractory period wherein no sensing is permitted, followed by a second or relative refractory period during which atrial sensing is permitted but the pacemaker is not permitted to respond to an atrial event sensed by the atrial sensing circuit. Hence, an atrial event sensed during the relative refractory period will not initiate an AV delay interval.

Unfortunately, the PVARP intended to prevent a PMT may lead to another rhythm referred to herein as a repetitive non-reentrant ventriculo-atrial synchronous (RNRVAS) rhythm. It is based on the ability of a patient's heart to sustain retrograde conduction and the coincidence of timing intervals in both the patient and the pacemaker. As with a PMT, an RNRVAS rhythm can be initiated by any phenomenon that would lead to AV disassociation and might trigger a PMT. A most common trigger mechanism is a premature ventricular contraction (PVC) which is generally defined as an R wave which occurs immediately succeeding a previous R wave or ventricular paced complex without an intervening P wave or atrial pacing pulse. A PMT is not initiated because the PVARP is programmed to a sufficient duration preventing the retrograde P wave from being tracked. However, if the pacing rate is high either due to a high programmed base rate or a physiologic sensor-driven rate being high, the atrial escape interval may time out and deliver an atrial pacing pulse at a time when the atrial myocardium is still physiologically refractory from the retrograde P wave. Hence, even though the atrial pacing output may be well above the atrial capture threshold, it will not capture the atria because it occurs at a time when the atrial myocardium is in its physiologic refractory period and cannot be depolarized. Hence, the RNRVAS rhythm results due to a combination of the high pacing rate and the non-detected retrograde P wave which causes the atrial tissue to not yet be recovered at a time when the atrial pacing pulse is delivered at the end of the atrial escape interval. A more detailed description of the manner in which the RNRVAS rhythm may be initiated follows subsequently in the detailed description of FIG. 3.

This rhythm is consistent with normal pacemaker function and represents a mismatch between the physiologic parameters of the patient's heart with the parametric settings of the pacemaker. The RNRVAS rhythm can result in significant symptoms such as a significant decrease in both blood pressure and cardiac output, palpitations, dizziness and lightheadedness.

SUMMARY OF THE INVENTION

The present invention provides a system and method for detecting and treating a repetitive non-reentrant ventriculo-atrial synchronous (RNRVAS) cardiac rhythm. The system and method are adapted for use in an implantable cardiac stimulation device including a pulse generator that delivers atrial and ventricular pacing stimulation pulses to a heart. The device provides the ventricular pacing pulses on demand an AV delay interval after at least an atrial pacing pulse and the atrial pacing pulses an atrial escape interval after a natural or paced ventricular event. In accordance with a broader aspect of the present invention, when an RNRVAS rhythm is detected, a therapy control circuit causes the pulse generator to deliver a secondary atrial pacing pulse following a primary atrial pacing pulse delivered at the end of an atrial escape interval.

The secondary atrial pacing pulse may be delivered before the end of the AV delay following the primary atrial pacing pulse, so that it is delivered at a time when the atria are fully recovered to capture the atria. The AV delay interval may then be reset by the secondary atrial pacing pulse.

The secondary atrial pacing pulse may alternatively be delivered after the AV delay interval and hence after the next ventricular pacing pulse. It will then render the atria refractory and prevent a retrograde P wave to terminate the RNRVAS rhythm.

If the secondary atrial pacing pulse is delivered before the end of the AV delay interval initiated by the primary atrial pacing pulse, the therapy control may further cause the pulse generator to deliver a tertiary atrial pacing pulse after the next ventricular pacing pulse. This again will render the atria refractory at a time when a retrograde P wave might otherwise be caused by a retrograde conduction. Once the RNRVAS rhythm is terminated, the atrial tertiary pulses may be withheld when the cardiac rate falls below a predetermined rate.

To detect an RNRVAS rhythm, the system may register an atrial-ventricular complex type for each cardiac cycle. The complex types preferably include AR complexes wherein atrial pacing pulses are followed by R waves and AV complexes wherein atrial pacing pulses are followed by ventricular pacing pulses. A change from an AR complex to an AV complex may denote a loss of atrial capture and hence may be used to detect an RNRVAS rhythm. A further criteria may include the condition that the cardiac rate be higher than a predetermined rate in addition to the AR complex to AV complex change.

The complex discrimination may be achieved by the system noting the delivery of the atrial and ventricular pacing pulses and the detection of R waves. Alternatively, the complex discrimination may be achieved through morphology detection capable of discerning a fully inhibited morphology and a fully paced morphology. Upon RNRVAS rhythm redetection, a morphology other than a fully paced morphology or a fully inhibited morphology would indicate a fusion beat and atrial capture with subsequent intact AV nodal conduction.

For patients with high degree AV block and who are therefore paced continually with AV complexes, the detection criteria may alternatively be an increase in cardiac rate to above a predetermined rate.

Still further, RNRVAS rhythm detection may be achieved by morphology detection of atrial revoked responses, atrial loss of capture, and atrial fusion beats. Here, if an atrial loss of capture determined through morphology detection is preceded by a ventricular pacing pulse, the RNRVAS rhythm may be declared and appropriate therapy initiated.

Still further, an RNRVAS rhythm may be detected by sensing atrial activity during the post ventricular atrial refractory period. A retrograde P wave occurring during this time will render the atria refractory requiring therapy to provide an atrial pacing pulse at a time when the atria are fully recovered. A further condition to this manner of detection may be the delivery of AV pacing complexes at a rate above a predetermined rate.

BRIEF DESCRIPTION OF THE DRAWINGS

Further features and advantages of the present invention may be more readily understood by reference to the following description taken in conjunction with the accompanying drawings, in which:

FIG. 3 is a schematic electrocardiogram illustrating the manner in which a repetitive non-reentrant ventriculo-atrial synchronous (RNRVAS) rhythm may be initiated;

FIG. 4 is a flow chart illustrating a first embodiment of the present invention for detecting an RNRVAS rhythm;

FIG. 5 is another flow chart illustrating a further embodiment of the present invention for detecting an RNRVAS rhythm;

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
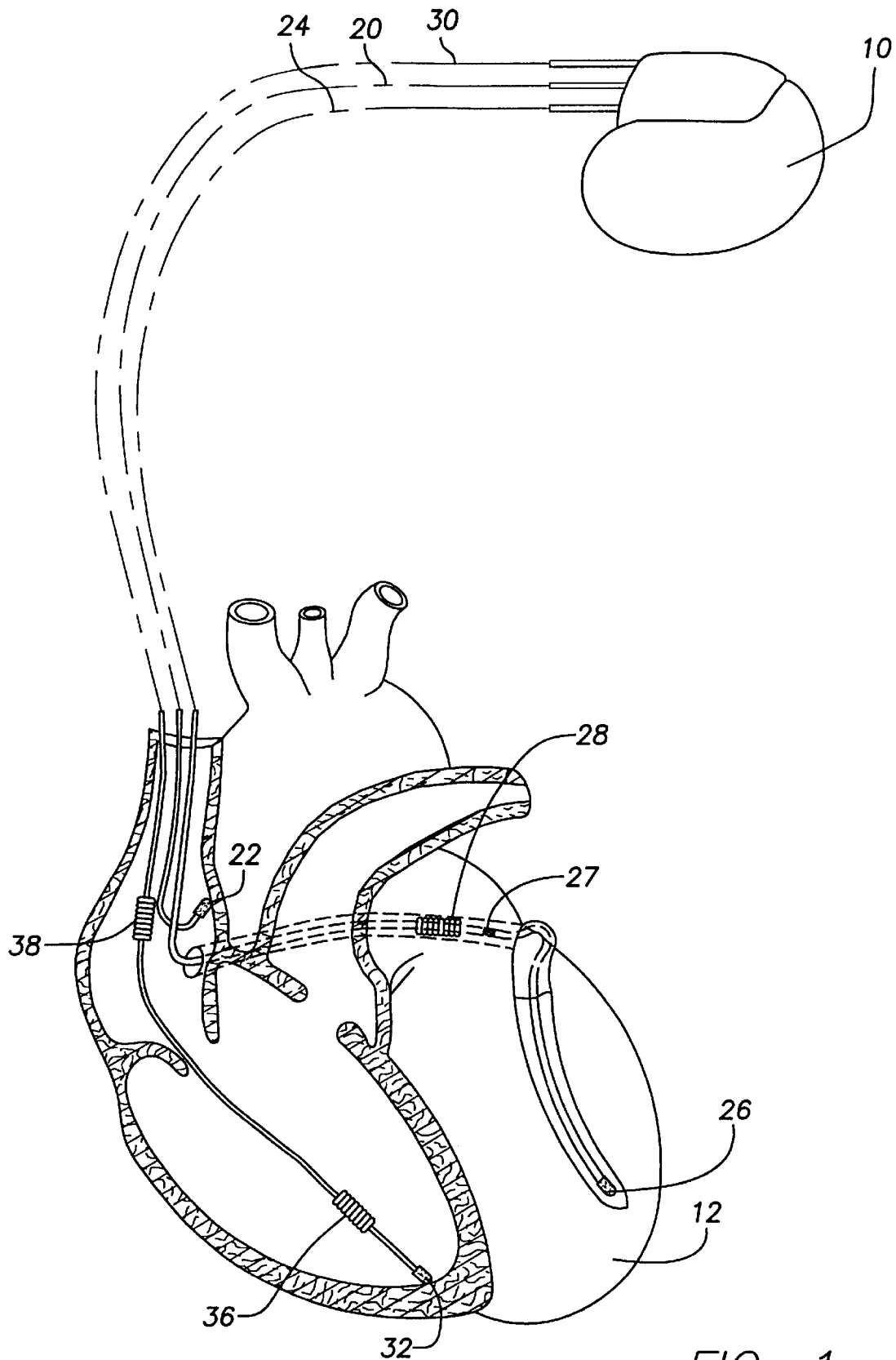
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of at least two leads, 20, 30 and possibly three-leads, 20, 24 and 30 or more suitable for delivering dual-chamber or multi-chamber stimulation and shock therapy. Three leads are only illustrative. There may be more or less but there must be at least one lead in the atrium and one in the ventricle. To sense atrial cardiac signals and to provide atrial chamber stimulation therapy, the stimulation device 10 is coupled to an implantable atrial lead 20 (illustrated as being positioned in the right atrium but also capable of being placed in the left atrium or in the coronary sinus to achieve left atrial stimulation) having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
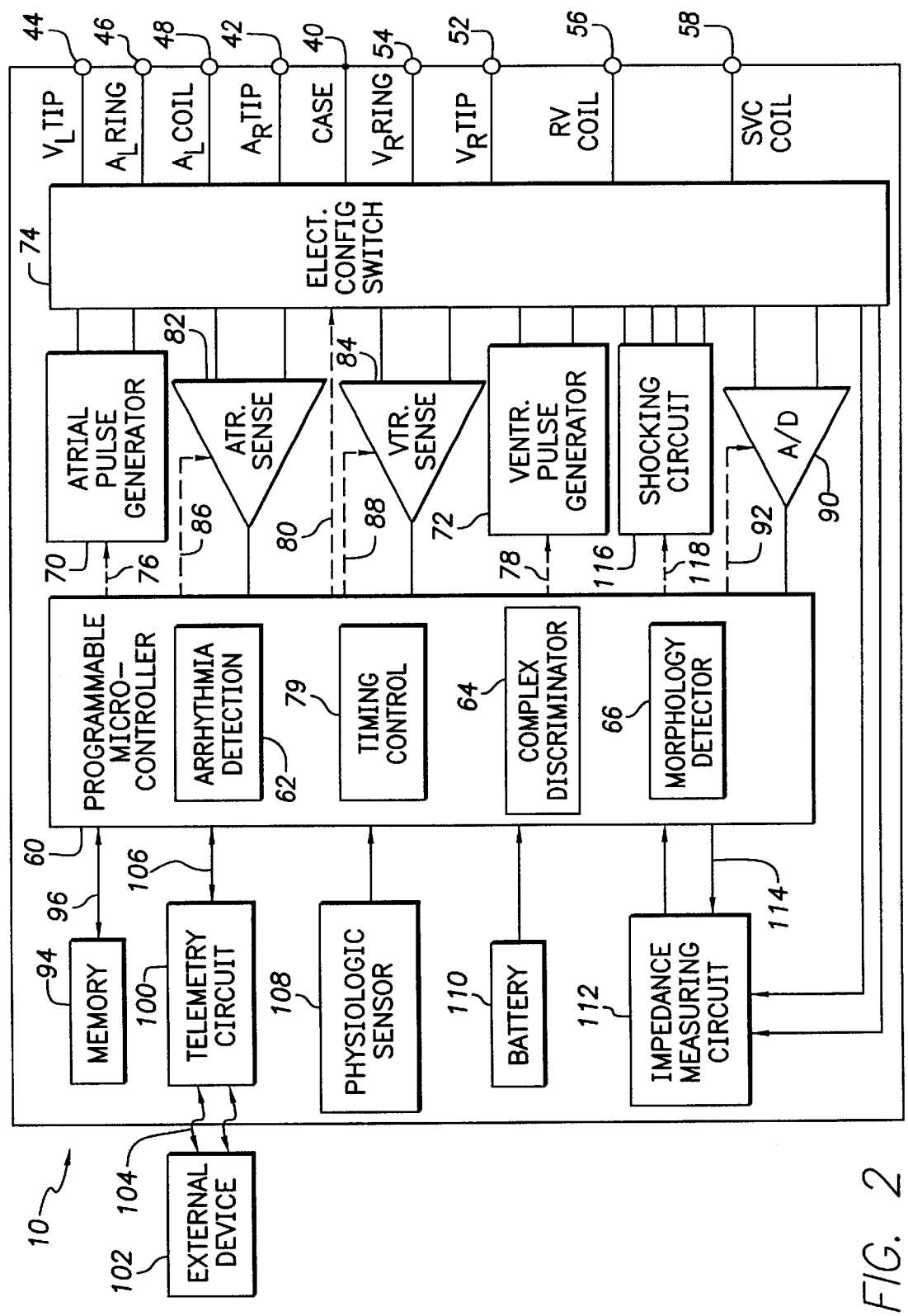
FIG. 2 is a functional block diagram of a multi-chamber implantable stimulation device illustrating the basic elements of a stimulation device which can provide cardioversion, defibrillation and pacing stimulation in four chambers of the heart and which embodies the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

At the core of the stimulation device 10 is a programmable microcontroller 60 which controls the various modes of stimulation therapy and which forms a therapy control circuit for treating repetitive non-reentrant ventriculo-atrial synchronous (RNRVAS) rhythms in accordance with the various embodiments of the present invention to be described subsequently. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial escape interval (VA) delay, atrial interconduction (A-A) delay, pause durations or ventricular interconduction (V-V) delay, etc.) as well as to keep track of the timing of refractory periods such as PVARP intervals, noise detection windows, evoked response windows, alert intervals, event marker timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic sensitivity control, bandpass filtering, and a threshold detection circuit, as known in the art, to selectively sense the cardiac signal of interest. The automatic sensitivity control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the sensitivity, threshold, polarization charge removal circuitry (not shown), and the timing of any blocking circuitry (not shown) coupled to the inputs of the sensing circuits, 82 and 84, as is known in the art.

For arrhythmia detection, the device 10 includes an arrhythmia detector 62 which utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude, determines if capture has occurred. Capture detection may occur on a beat-by-beat basis or on a sampled basis.

The controller 60 further includes a complex discriminator 64. The complex discriminator 64 discriminates and registers various atrioventricular complexes by monitoring the sequence of delivered pacing pulses and sensed cardiac events (P waves and R waves). Among the complexes registered are AV complexes and AR complexes. An AV complex is a pacing sequence of an atrial pacing pulse followed by a ventricular pacing pulse. An AR complex is a sequence of an atrial pacing pulse followed by a sensed R wave.

In accordance with the present invention, the arrhythmia detection monitors a series of complexes. It detects repetitive non-reentrant ventriculo-atrial synchronous (RNRVAS) rhythms when a change occurs from an AR complex to an AV complex. A further condition to such detection may also include a relatively high cardiac rate, such as a rate above 90 PPM, for example. A change from AR complexes to an AV complex, as will be seen hereinafter, may be an indicator of loss of atrial capture and the presence of an RNRVAS rhythm in need of attention. For some patients, especially those with high grade AV block, which are continually paced with AV complexes, an RNRVAS rhythm may develop when the cardiac rate exceeds a predetermined or programmable rate, such as 90 PPM, for example if this patient is also prone to retrograde conduction.

As may also be noted in FIG. 2, the controller 60 further includes a morphology detector 66. Morphology detection can be a very useful tool in detecting an RNRVAS rhythm. Morphology detection is well known in the art and can be employed for discerning fully paced ventricular beats, intrinsic ventricular activation or ventricular fusion, atrial loss of capture, an atrial evoked response, or an atrial fusion beat. The morphology detector may utilize the electrograms provided by the acquisition system 90.

For RNRVAS rhythm detection, the morphology detector may be employed by the arrhythmia detector 62 to determine if an atrial loss of capture occurs following effective atrial and ventricular pacing pulses. If this condition exists it may indicate that the loss of capture was due to the atria being refractory due to a retrograde P wave and require RNRVAS rhythm intervention.

Morphology detection may also be useful in RNRVAS rhythm redetection. Hence, following RNRVAS intervention AV pacing, if the ventricular morphology is other than either a fully paced morphology, e.g., a fully inhibited morphology or a fusion morphology, it may be presumed that atrial capture has been restored and the RNRVAS rhythm terminated.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 108, commonly referred to as a "rate-responsive" sensor because it is typically used to adjust pacing stimulation rate according to the exercise state or other physiologic stress of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse, The battery 110 must also have a predictable discharge characteristic so that elective replacement time can be detected. Accordingly, the device 10 employs lithium/silver vanadium oxide batteries, as is true for many such devices to date.

If it is the primary function of the device 10 to function as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Referring now to FIG. 3, it illustrates a schematic electrocardiogram 120 illustrating the manner in which an RNRVAS rhythm may be initiated. As will be noted, the electrogram 120 begins with an AR complex including an effective atrial pacing pulse 122 followed by an R wave 124. The successful atrial pacing pulse 122 renders the atria refractory during a physiologic atrial refractory period 126. Upon the sensing of the R wave 124, a post ventricular atrial refractory period (PVARP) 128 is initiated by the device. As is will known in the art, the PVARP may be divided into a first portion wherein the atrial sense amplifiers are precluded from sensing any cardiac activity and a second portion wherein the atrial sense amplifiers are permitted to sense cardiac activity but the device is not permitted to react to such sensed activity. The second refractory portion is often referred to as the relative post ventricular atrial refractory period.

The next cardiac event is a premature ventricular contraction (PVC) 130. The sensing of the PVC initiates another PVARP 132. Following the PVC 130 is a retrograde P wave 134. As will be noted in FIG. 3, the retrograde P wave occurs during the PVARP 132 and as a result, the device does not react to the retrograde P wave 134. The retrograde P wave 134 does render the atria refractory by initiating a physiologic atrial refractory period 136. The cardiac rate is high enough so that at the end of the atrial escape interval initiated by the PVC 130, an atrial pacing pulse 138 is delivered during the physiologic atrial refractory period 136. This renders the atrial pacing pulse 138 ineffective to capture the atrial and therefore results in functional loss of atrial capture.

The atrial pacing pulse 138 initiates an AV delay interval resulting in a delivered ventricular pacing pulse 140 at the end of the AV delay interval. The ventricular pacing pulse 140 causes a ventricular evoked response 142 and the initiation of another PVARP 144. The evoked response 142 in turn results in another retrograde P wave 146 which occurs during the PVARP 144 and renders the atria refractory for another physiologic atrial refractory period 148. At the end of the atrial escape interval initiated by the ventricular pacing pulse 140, another atrial pacing pulse 150 is delivered which is rendered ineffective because it occurs during the physiologic atrial refractory period 148.

By this time, the RNRVAS rhythm has become fully initiated and established. Of particular importance is the fact that the RNRVAS rhythm became established even though the device was functioning properly in a "normal" manner resulting from a mismatch between the physiologic characteristics of the patient and the parametric settings of the device.

The RNRVAS rhythm will continue with significant symptoms such as, for example, reduction in cardiac output, palpitations, dizziness and/or pulmonary congestion with shortness of breath and is thus in need of immediate treatment.

FIG. 4 is a flow diagram which illustrates a manner in which an RNRVAS rhythm may be detected in accordance with one embodiment of the present invention. The process of FIG. 4 initiates with an activity block 160 wherein the atrial-ventricular complexes are registered in a manner as previously described. After a current complex is registered in accordance with activity step 160, the process advances to a decision block 162 wherein the arrhythmia detector 62 determines if there has been a change from AR pacing to AV pacing. If there has not been such a change in the atrial-ventricular complexes, the process returns. However, if there has been such a change, the process advances to decision block 164 wherein it is determined if the cardiac rate is greater than a predetermined or programmable rate, such as, for example, 90 PPM. If the rate is not above the predetermined rate, the process returns. However, if the rate is above the predetermined rate, the process has detected an RNRVAS rhythm.

The foregoing is consistent with the electrogram of FIG. 3. There it will be noted that there was a change from an AR complex to an AV complex. The change from the AR complex to the AV complex was the result of disassociated cardiac activity in the form of the PVC 130 resulting in a retrograde P wave 134 during the PVARP 132. The retrograde P wave 134 caused the atria to be refractory during the physiologic atrial refractory period 136 during which the atrial escape interval ended resulting in an ineffective atrial pacing pulse 138. Hence, the pacing pulse 138 was rendered ineffective by the physiologic atrial refractory period 136 resulting in loss of atrial capture and the initiation of the RNRVAS rhythm.

FIG. 5 illustrates another flow chart showing another manner in which an RNRVAS rhythm may be detected. Here, the process begins with a decision block 166 wherein the arrhythmia detector 62 determines if an atrial event is detected during the PVARP. This would correspond to, for example, the retrograde P wave 134 of FIG. 3 occurring during the PVARP 132. If an atrial event is not sensed during a PVARP, the process returns. However, if an atrial event is sensed during a PVARP as illustrated in FIG. 3, the process advances to activity block 168 wherein the arrhythmia detector determines if the cardiac rate is greater than the predetermined rate of, for example, 90 PPM. If the rate is less than 90 PPM, the process returns. However, if the rate is greater than 90 PPM, an RNRVAS rhythm is declared as being possible and the process completes with the detection of an RNRVAS rhythm.

Figure 6:
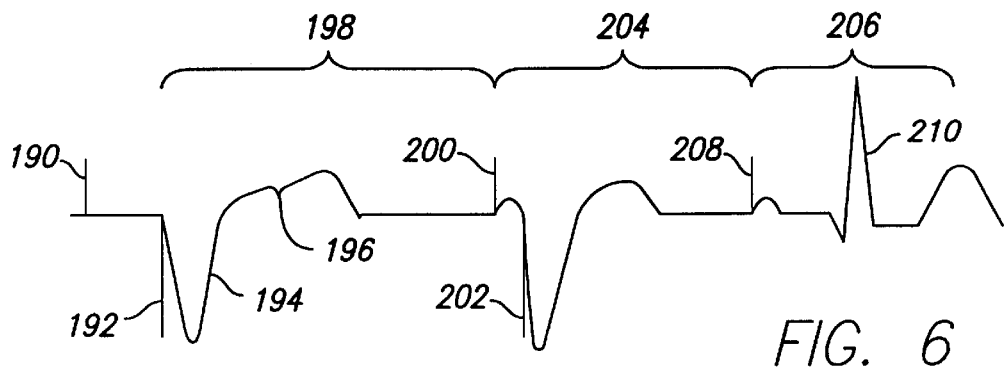
FIG. 6 is a schematic electrocardiogram illustrating the manner in which the RNRVAS rhythm may be terminated using atrial escape interval extension in accordance with an embodiment of the present invention.
Figure 7:
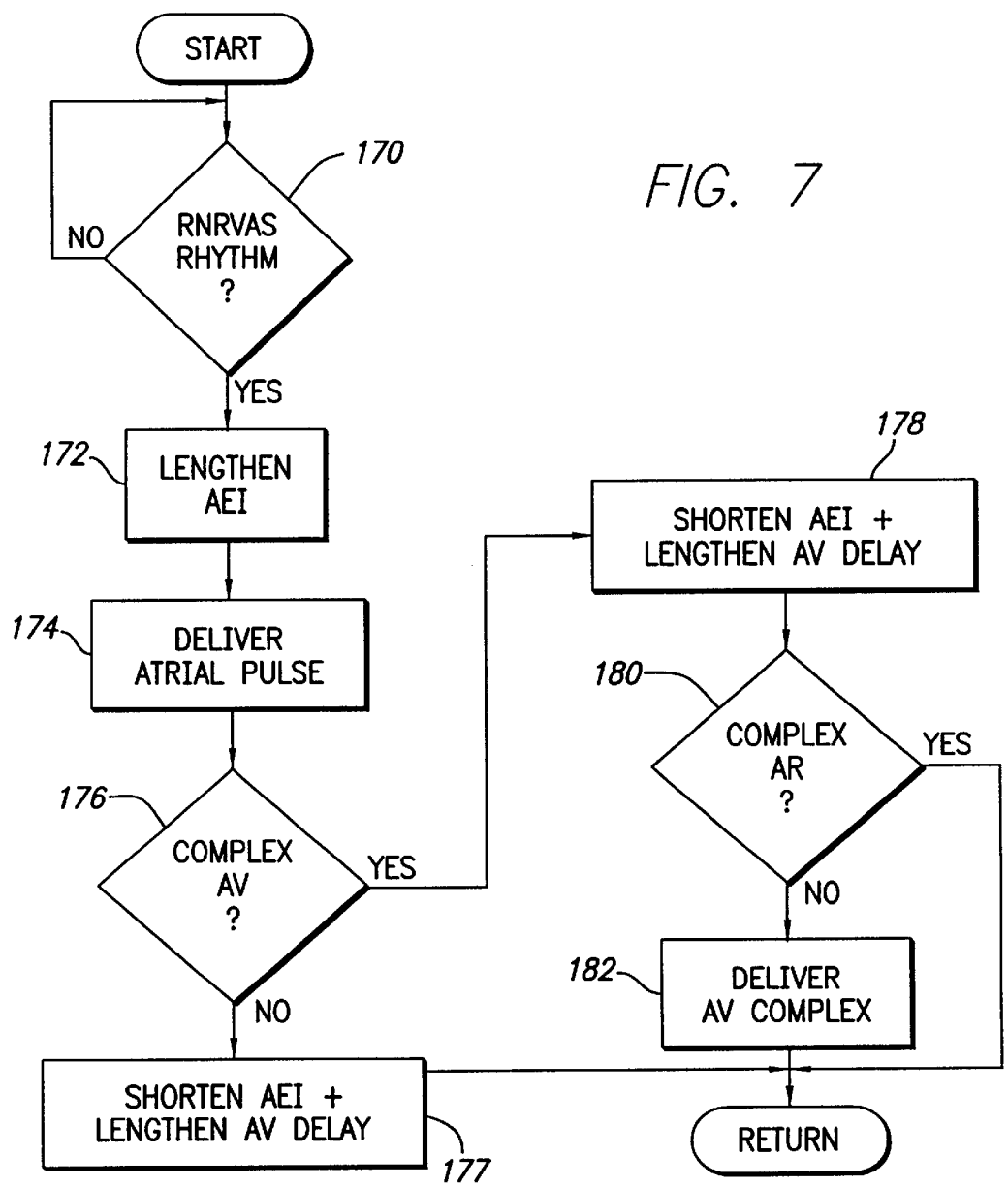
FIG. 7 is a flow chart illustrating process steps which may be implemented to terminate the RNRVAS rhythm shown in FIG. 6 in accordance with one embodiment of the present invention.

Referring now to FIGS. 6 and 7, FIG. 6 is a schematic electrocardiogram illustrating the manner in which therapy may be applied in accordance with the method process steps illustrated in the flow chart of FIG. 7. The process of FIG. 7 initiates with a decision block 170 wherein it is determined if an RNRVAS rhythm has been detected. If not, the process returns. However, if an RNRVAS rhythm has been detected, the process then advances to an activity block 172. In FIG. 6, it will be observed that the first atrial-ventricular complex illustrated is an AV complex including an ineffective atrial pacing pulse 190 and a subsequent ventricular pacing pulse 192 delivered an AV delay after the atrial pacing pulse 190. The ventricular pacing pulse 192 results in an evoked response 194 which in turn causes a retrograde P wave 196. The RNRVAS rhythm illustrated in FIG. 6 may be detected by either the process of FIG. 4 or the process of FIG. 5. The process of FIG. 4, assuming an AR complex prior to the illustrated AV complex, would cause detection of the RNRVAS rhythm by noting the change from the AR complex to the AV complex at a rate greater than the predetermined rate.

In accordance with FIG. 5, the retrograde P wave 196 would be sensed during the PVARP and with a cardiac rate greater than the predetermined rate. This also would result in the detection of the RNRVAS complex.

Upon the determination in decision block 170 that an RNRVAS rhythm has been detected, the activity block 172 initiates RNRVAS rhythm therapy. In accordance with activity block 172, the atrial escape interval (AEI) or VA interval is immediately lengthened to result in a lengthened VA interval 198 as illustrated in FIG. 6. This allows more time for the atria to recover from the retrograde P wave 196 before the next atrial pacing pulse is delivered. Simultaneously with the lengthening of the VA delay in accordance with step 172, the following AV delay is preferably decreased by the same amount so that the effective ventricular pacing rate remains the same.

Following activity block 172, the atrial pulse generator 70 is caused to deliver an atrial pacing pulse at the end of the lengthened atrial escape interval 198 in accordance with activity block 174. Because the atrial escape interval was lengthened, the atria have had sufficient time to recover to enable the atrial pacing pulse 200 to be effective in capturing the atria. Following the atrial pacing pulse 200, the device in accordance with its normal operation is caused to deliver a ventricular pacing pulse 202 on demand (if required) at the end of the shortened AV delay.

After the device has had sufficient time to deliver a ventricular pacing pulse if required, such as after the shortened AV delay interval, the process advances to a decision block 176 wherein it is determined if the last complex was an AV complex. In all likelihood, due to the shortened AV delay, the complex will be an AV complex. However, if the complex is not an AV complex, an AR complex will be assumed indicating the termination of the RNRVAS rhythm. In this event, the process proceeds to activity block 177 to shorten the AEI or VA interval and lengthen the AV delay to normal programmed or sensor driven values. The process then returns.

If the last complex is determined in decision block 176 to have been an AV complex, the process then advances to activity block 178 wherein the AEI or VA interval is shortened and the AV delay is lengthened by the same amount. This may be seen in FIG. 6 wherein the shortened VA interval results in the escape interval 204 and the lengthened AV delay results in the lengthened AV delay 206. At this time, the process waits for the device to deliver the atrial pacing pulse 208 at the end of the shortened atrial escape interval 204 and to either apply a ventricular pacing pulse at the end of the lengthened AV delay 206 or sense an R wave occurring before the end of the lengthened AV delay 206. The process then advances to decision block 180 where it determines if the last complex was an AR complex. As will be noted in FIG. 6, the complex is an AR complex including the atrial pacing pulse 208 and a sensed R wave 210 occurring before the end of the lengthened AV delay 206. As a result, the electrocardiogram returned to an AR complex and the process returns after having successfully terminated the RNRVAS rhythm. However, if the last complex was not an AR complex, the process then advances to activity block 182 wherein the device is caused to deliver an AV complex to the heart with the maximum possible atrial escape interval and the shortest possible AV delay. Since this represents the best chance of terminating the unterminated RNRVAS rhythm, the process, once having completed activity block 182, returns to the programmed AV delay at the pre-set or sensor-driven AV pacing rate. Alternatively, after completing activity block 181, the process would return to repeat blocks 178, 180 and 182. Here, activity block 178 may be carried out by adjusting the VA delay to a value intermediate the maximum allowed value and the value used in activity block 178 while maintaining the ventricular rate.

Figure 8:
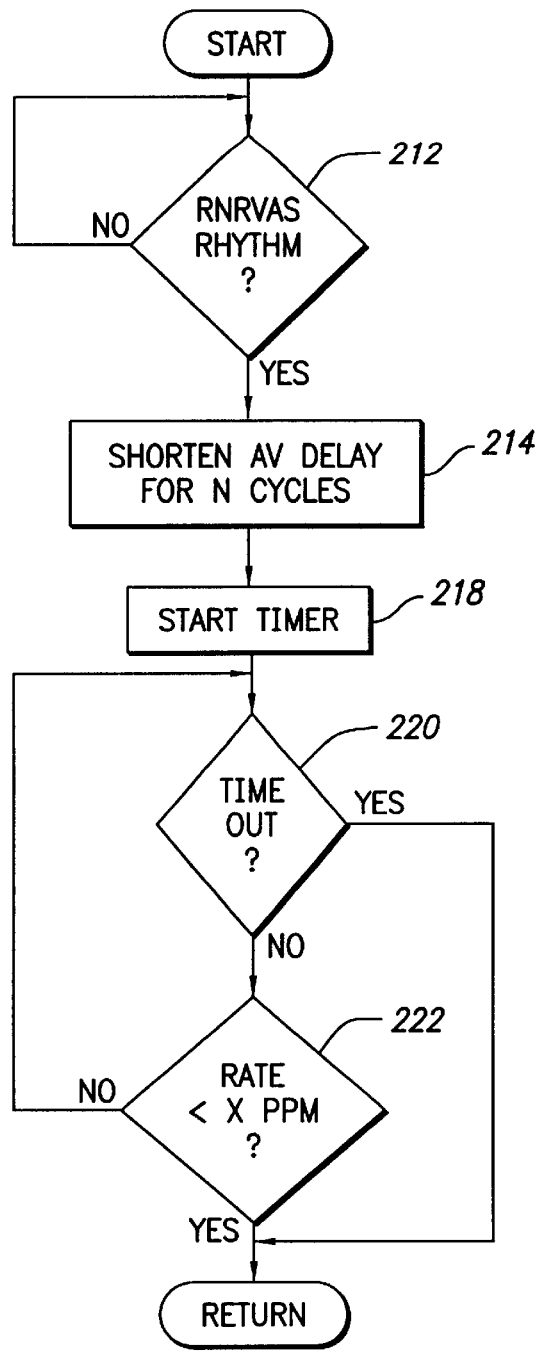
FIG. 8 is another flow diagram illustrating another RNRVAS rhythm therapy in accordance with further aspects of the present invention.

Referring now to FIG. 8, it is a flow chart illustrating another manner in which an RNRVAS rhythm may be terminated in accordance with a further embodiment of the present invention. The process of FIG. 8 is particularly adapted for those patients having high grade AV block such that their basic paced rhythm will be an AV rhythm all the time while being capable of retrograde conduction and hence, can develop an RNRVAS rhythm. The process initiates at decision block 212 wherein it is determined if an RNRVAS rhythm has been detected. Since in these patients there will be continuous AV complexes, the RNRVAS rhythm may be detected by noting the cardiac rate and if the AV paced rate exceeds a detection rate, the possibility of an RNRVAS rhythm is declared. If an RNRVAS rhythm is suspected, the process immediately advances to activity block 214 wherein the AV delay interval is shortened and the atrial escape interval is lengthened by the same amount for N cycles. The number of cycles in which this occurs may be as few as one cycle but may be more than one cycle.

After the N number of cycles, the process then advances to activity block 218. As the rhythm will still be an AV paced rhythm, the process pauses with the starting of a timer of the timing control circuit 79 of FIG. 2 at activity block 218. This initiates a pause which extends for either a predetermined period of time or until the cardiac rate falls below a predetermined rate such as the detection rate which may be, for example, 90 PPM. To that end, the process advances to decision block 220 where it is determined if the timer started in activity block 218 has timed out. If the timer has timed out, the process returns. However, if the timer has not timed out the process advances to decision block 222 wherein it is determined if the cardiac rate has fallen below the predetermined rate. If the rate has not fallen below the predetermined rate, the process then returns to decision block 220. However if the rate has fallen below the predetermined rate, the process returns with the system primed to again to attempt termination of the next RNRVAS rhythm to be detected or to attempt termination of the current RNRVAS rhythm if it has persisted.

Figure 9:
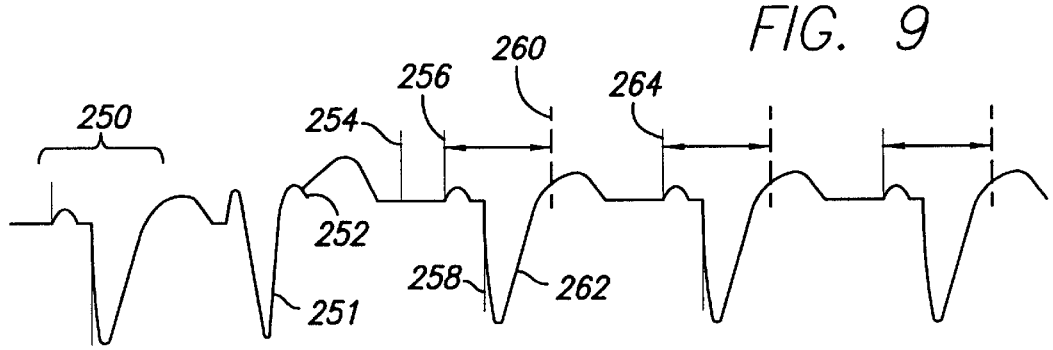
FIG. 9 is a schematic electrocardiogram illustrating the manner in which the RNRVAS rhythm may be terminated using secondary atrial pacing pulses in accordance with a further embodiment of the present invention.
Figure 10:
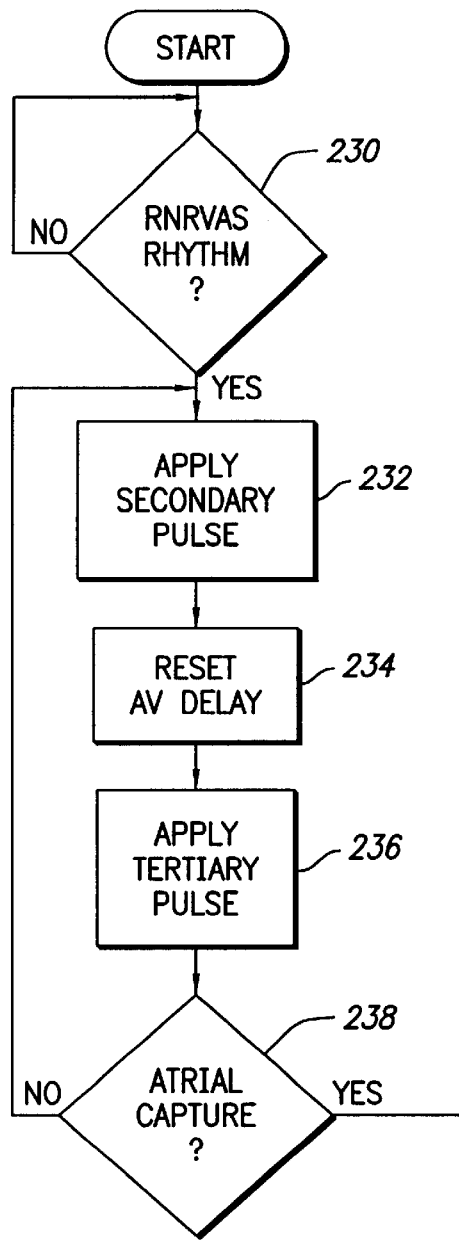
FIG. 10 is a flow chart illustrating process steps which may be implemented to terminate the RNRVAS rhythm shown in FIG. 9 in accordance with another embodiment of the present invention.
Figure 10:
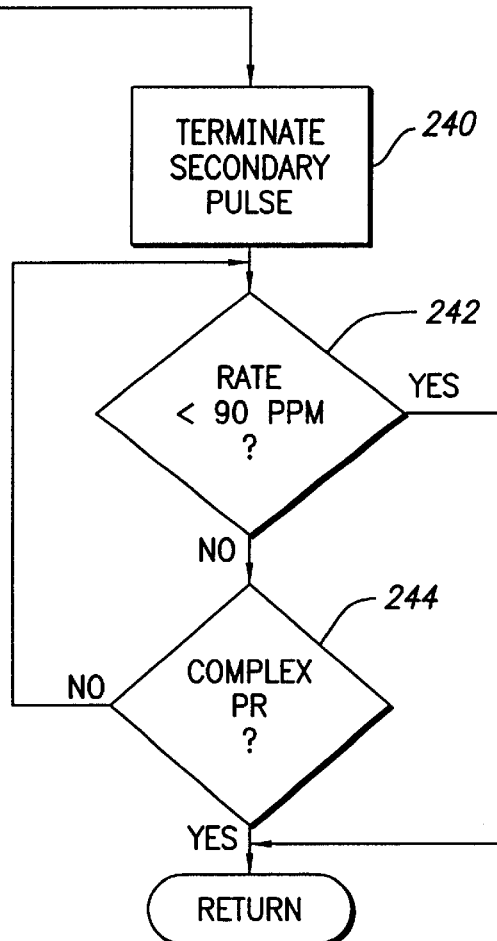

Referring now to FIGS. 9 and 10, FIG. 9 is a schematic electrocardiogram illustrating the manner in which an RNR-VAS rhythm may be terminated in accordance with the method process steps illustrated in the flow chart of FIG. 10. Here, the RNRVAS rhythm is terminated through the use of secondary atrial pacing pulses without modification of the atrial escape intervals although the AV delay interval for this first cycle is significantly increased.

The process initiates at decision block 230 wherein it is determined if an RNRVAS rhythm is likely as it occurs above a programmed or predetermined AV paced rate. Complex 250 represents AV pacing at a rate above a predetermined rate. The PVC 251 is associated with retrograde conduction resulting in retrograde P wave 252. Sensing of a retrograde P wave 252 during a PVARP, or, detecting an ineffective atrial pacing pulse 254 on the next cycle through morphology detection or atrial AutoCapture identifies the setting for development of RNRVAS. Regardless of the manner of detection, once this combination of events that may result in an RNRVAS rhythm is detected, the process then advances to activity block 232 wherein the atrial pulse generator 70 is caused to deliver a secondary atrial pacing pulse 256 before the end of the AV delay following the primary atrial pacing pulse 254. Preferably, the secondary atrial pacing pulse 256 is applied 100 to 250 milliseconds after the atrial pacing pulse 254. The scheduled delivery of the ventricular output pulse 258 is delayed by a programmable value ranging from 0 ms (delivered on time with respect to the programmed AV delay) to the maximum AV delay allowed by the system, these intervals starting with the back-up atrial output pulse 256.

While the atrial pacing pulse 254 was ineffective to capture the atria because of being applied during the physiologic atrial refractory period of the heart, the secondary atrial pacing pulse 256 is effective in capturing the atria because it is applied at a time when the atria are fully recovered from the retrograde P wave 252.

Once the secondary pacing pulse 256 is delivered, the process immediately advances to activity block 234 wherein the AV delay is reset from the secondary atrial pacing pulse 256. The reset AV delay between atrial output 256 and ventricular output 258 is a programmable value capable of being programmed from 0 ms to the maximum allowed interval. The device is now permitted to deliver a ventricular pacing pulse 258 in accordance with normal operation and thereafter, the process continues to activity block 236 wherein a tertiary atrial pacing pulse 260 is delivered. The tertiary atrial pacing pulse is delivered during or shortly after the evoked response 262 to the ventricular pacing pulse 258 to preclude a retrograde conduction of the evoked response 262 which otherwise may cause a retrograde P wave. The tertiary atrial pacing pulse may be applied, for example, between 300 and 350 milliseconds after the secondary atrial pacing pulse.

Once the atrial tertiary pulse is applied, the device is permitted to deliver an atrial pacing pulse 264 at the end of its escape interval in accordance with normal operation. Once the atrial pacing pulse 264 is delivered, the process then advances to decision block 238 to determine if the pacing pulse 264 has captured the atria based on atrial morphology or evoked response detection consistent with atrial AutoCapture. If it failed to capture the atria, the process returns to step 232 to apply another secondary atrial pacing pulse. However, if the atrial pacing pulse 264 captured the atria as illustrated, the process then advances to activity block 244 wherein the delivery of the secondary atrial pacing pulses is terminated.

The device is then permitted to pace the heart normally. This operation continues until either the cardiac rate falls below a predetermined rate of, for example, 90 PPM as determined in decision block 242 or until a complex is registered that is a PR complex in accordance with decision block 244. When either of these two conditions is satisfied, the process returns to permit normal pacing operation of the device.

Figure 11:
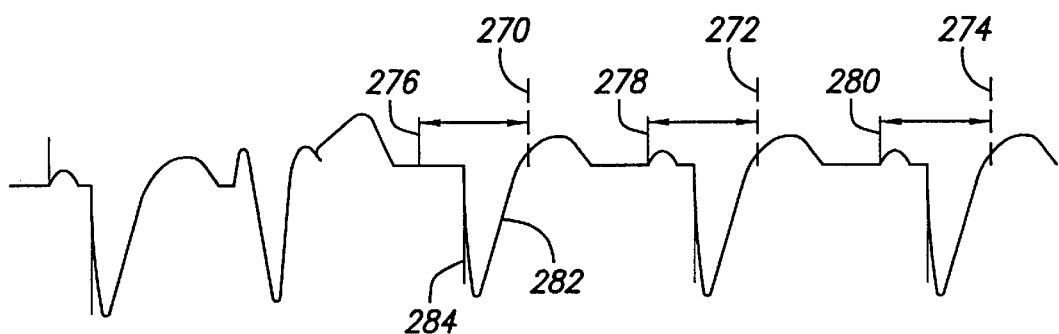
FIG. 11 is another schematic electrocardiogram illustrating a further embodiment of the present invention for terminating an RNRVAS rhythm utilizing secondary atrial pacing pulses.

Referring now to FIG. 11, it illustrates an electrogram showing the manner in which an RNRVAS rhythm may be terminated in accordance with a further embodiment of the present invention. As will be noted in FIG. 11, the RNRVAS rhythm is terminated by the delivery of secondary pulses 270, 272, and 274 following corresponding atrial primary pulses 276, 278, and 280, respectively. Preferably, the secondary atrial pacing pulses are delivered between 200 to 350 milliseconds after the corresponding primary atrial pacing pulses without any change in the AV paced interval. The secondary atrial pacing pulses will commonly be delivered coincident with the paced QRS complex 282. The secondary atrial pacing pulses 270, 272, and 274, are delivered to render the atrial myocardium physiologically refractory. This will block retrograde P waves. It is essential that these secondary pulses be sufficiently far from the scheduled atrial output pulses 276, 278 and 280 to allow time for the atrial tissue to physiologically recover so that the scheduled atrial output pulses 276, 278 and 280 will effectively capture the atrium. The first such secondary atrial pacing pulse 270, by blocking the retrograde P wave which may have occurred due to the evoked response 282 from the ventricular pacing pulse 284 permits the following primary atria pacing pulse 278 to capture the atria to restore AV synchrony and hence terminate the RNRVAS rhythm. The application of the secondary atrial pacing pulses is preferably discontinued after a programmable number of consecutive cycles (N).

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac stimulation device including a pulse generator that delivers atrial and ventricular pacing stimulation pulses to a heart, each ventricular pacing pulse being delivered on demand an AV delay after at least an atrial pacing pulse, and the atrial pacing pulses being delivered an atrial escape interval after a natural or paced ventricular event, a system for treating a repetitive non-reentrant ventriculo-atrial synchronous (RNRVAS) cardiac rhythm, the system comprising:

a sensing circuit that senses cardiac activity of the heart;
a detector responsive to the sensing circuit that determines if a repetitive non-reentrant ventriculo-atrial synchronous rhythm is present; and
a therapy control circuit that causes the pulse generator to deliver a secondary atrial pacing pulse following a primary atrial pacing pulse delivered at the end of an atrial escape interval responsive to the detector determining that a repetitive non-reentrant ventriculo-atrial synchronous rhythm is present.

2. The system of claim 1 wherein the therapy control circuit causes the pulse generator to deliver the secondary atrial pacing pulse bout 100 to 150 milliseconds after the primary atrial pacing pulse.

3. The system of claim 2 wherein the device provides a post ventricular atrial refractory period and wherein the detector determines that a repetitive non-reentrant ventriculo-atrial synchronous rhythm is present responsive to the sensing circuit sensing cardiac activity during the post ventricular atrial refractory period.

4. The system of claim 1 further including an atrial evoked response detector that detects atrial evoked responses following atrial pacing pulses and wherein the detector is responsive to the atrial evoked response detector failing to detect an atrial evoked response to determine the presence of a repetitive non-reentrant ventriculo-atrial synchronous rhythm.

5. The system of claim 4 wherein the atrial evoked response detector is a morphology detector.

6. The system of claim 4 wherein the atrial evoked response detector includes a morphology detector that discriminates an atrial evoked response, a fusion, and an atrial loss of capture and wherein the detector determines that an repetitive non-reentrant ventriculo-atrial synchronous rhythm is present if an atrial loss of capture is preceded by a ventricular pacing pulse.

7. They system of claim 4 further including a cardiac rate detector and wherein the detector is responsive to the cardiac rate being above a given rate and the atrial evoked response detector to determine the presence of a repetitive non-reentrant ventriculo-atrial synchronous rhythm.

8. The system of claim 1 wherein the therapy control circuit resets the AV delay following the secondary pacing pulse.

9. The system of claim 1 wherein the therapy control circuit causes the pulse generator to deliver a tertiary atrial pacing pulse following the secondary pulse.

10. The system of claim 9 wherein the therapy control circuit causes the pulse generator to deliver the tertiary atrial pacing pulse after a ventricular event following the secondary atrial pacing pulse.

11. The system of claim 9 wherein the tertiary atrial pacing pulse is delivered about 200 to 350 milliseconds after the secondary atrial pacing pulse.

12. The system of claim 9 further including a cardiac rate detector that detects cardiac rate and wherein the therapy control circuit causes the pulse generator to terminate delivery of the tertiary atrial pacing pulses when the cardiac rate is below a predetermined rate.

13. The system of claim 9 further including a complex discriminator that determines an atrio-ventricular complex type for each cardiac cycle of the heart including an AR complex wherein an atrial pacing pulse is followed by an R wave and a PR complex wherein an intrinsic atrial event is followed by an R wave and wherein the therapy control circuit is responsive to an AR complex or a PR complex to cause the pulse generator to terminate delivery of the tertiary atrial pacing pulses.

14. The system of claim 1 wherein the therapy control circuit causes the pulse generator to deliver the secondary atrial pacing pulse after a ventricular event following the primary atrial pacing pulse.

15. The system of claim 1 wherein the therapy control circuit causes the pulse generator to deliver the secondary atrial pacing pulse about 200 to 350 milliseconds after the primary atrial pacing pulse.

16. In an implantable cardiac stimulation device including a pulse generator that delivers atrial and ventricular pacing stimulation pulses to a heart, each ventricular pacing pulse being delivered on demand an AV delay after at least an atrial pacing pulse, and the atrial pacing pulses being delivered an atrial escape interval after a natural or paced ventricular event, a system for treating a repetitive nonreentrant ventriculo-atrial synchronous cardiac rhythm, the system comprising:

sensing means for sensing cardiac activity of the heart;

rhythm detecting means responsive to the sensing means for detecting a repetitive non-reentrant ventriculo-atrial synchronous rhythm; and a therapy control means for causing the pulse generator to deliver a secondary atrial pacing pulse following a primary atrial pacing pulse delivered at the end of an atrial escape interval responsive to the detecting means detecting a repetitive non-reentrant ventriculo-atrial synchronous rhythm.

17. The system of claim 16 wherein the therapy control means causes the pulse generator to deliver the secondary atrial pacing pulse about 100 to 150 milliseconds after the primary atrial pacing pulse.

18. The system of claim 17 wherein the device provides a post ventricular atrial refractory period and wherein the rhythm detecting means detects a repetitive non-reentrant ventriculo-atrial synchronous rhythm responsive to the sensing means sensing cardiac activity during the post ventricular atrial refractory period.

19. The system of claim 16 further including an atrial evoked response detecting means for detecting atrial evoked responses following atrial pacing pulses and wherein the rhythm detecting means is responsive to the atrial evoked response detecting means failing to detect an atrial evoked response for detecting a repetitive non-reentrant ventriculo-atrial synchronous rhythm.

20. The system of claim 19 wherein the atrial evoked response detecting means includes a morphology detector.

21. The system of claim 19 wherein the atrial evoked response detecting means includes morphology detecting means for discriminating an atrial evoked response, a fusion, and an atrial loss of capture and wherein the rhythm detecting means detects a repetitive non-reentrant ventriculo-atrial synchronous rhythm when an atrial loss of capture is preceded by a ventricular pacing pulse.

22. The system of claim 19 further including cardiac rate detecting means and wherein the rhythm detecting means is responsive to the cardiac rate being above a given rate and the atrial evoked response detecting means for detecting a repetitive non-reentrant ventriculo-atrial synchronous rhythm.

23. The system of claim 16 wherein the therapy control means includes means for resetting the AV delay following the secondary pacing pulse.

24. The system of claim 16 wherein the therapy control means causes the pulse generator to deliver a tertiary atrial pacing pulse following the secondary pulse.

25. The system of claim 24 wherein the therapy control means causes the pulse generator to deliver the tertiary atrial pacing pulse after a ventricular event following the secondary atrial pacing pulse.

26. The system of claim 24 wherein the tertiary atrial pacing pulse is delivered about 200 to 350 milliseconds after the secondary atrial pacing pulse.

27. The system of claim 24 further including cardiac rate detecting means for detecting cardiac rate and wherein the therapy control means causes the pulse generator to terminate delivery of the tertiary atrial pacing pulses when the cardiac rate is below a predetermined rate.

28. The system of claim 24 further including complex discriminating means for determining an atrio-ventricular complex type for each cardiac cycle of the heart including an AR complex wherein an atrial pacing pulse is followed by an R wave and a PR complex wherein an intrinsic atrial event is followed by an R wave and wherein the therapy control means is responsive to an AR complex or a PR complex for causing the pulse generator to terminate delivery of the tertiary atrial pacing pulses.

29. The system of claim 16 wherein the therapy control means causes the pulse generator to deliver the secondary atrial pacing pulse after a ventricular event following the primary atrial pacing pulse.

30. The system of claim 16 wherein the therapy control means causes the pulse generator to deliver the secondary atrial pacing pulse about 200 to 350 milliseconds after the primary atrial pacing pulse.

31. In an implantable cardiac stimulation device including a pulse generator that delivers atrial and ventricular pacing stimulation pulses to a heart, each ventricular pacing pulse being delivered on demand an AV delay after at least an atrial pacing pulse, and the atrial pacing pulses being delivered an atrial escape interval after a natural or paced ventricular event, a method treating a repetitive non-reentrant ventriculo-atrial synchronous cardiac rhythm, the method including the steps of:

sensing cardiac activity of the heart to provide an electrogram signal;

responsive to the electrogram signal, detecting a repetitive non-reentrant ventriculo-atrial synchronous rhythm; and providing therapy including the step of causing the pulse generator to deliver a secondary atrial pacing pulse following a primary atrial pacing pulse delivered at the end of an atrial escape interval after detecting a repetitive non-reentrant ventriculo-atrial synchronous rhythm.

32. The method of claim 31 wherein the therapy providing step includes the step of causing the pulse generator to deliver the secondary atrial pacing pulse about 100 to 150 milliseconds after the primary atrial pacing pulse.

33. The method of claim 32 wherein the device provides a post ventricular atrial refractory period and wherein the detecting step includes detecting a repetitive non-reentrant ventriculo-atrial synchronous rhythm upon sensing cardiac activity during the post ventricular atrial refractory period.

34. The method of claim 31 further including the step of detecting atrial evoked responses following atrial pacing pulses and wherein the detecting step includes detecting a repetitive non-reentrant ventriculo-atrial synchronous rhythm upon failing to detect an atrial evoked response.

35. The method of claim 34 wherein the atrial evoked response detecting step includes detecting morphology.

36. The method of claim 34 wherein the atrial evoked response detecting step including detecting morphology to discriminate an atrial evoked response, a fusion, and an atrial loss of capture and wherein the detecting step detects an repetitive non-reentrant ventriculo-atrial synchronous rhythm if an atrial loss of capture is preceded by a ventricular pacing pulse.

37. The method of claim 34 further including the step of detecting cardiac rate and wherein the detecting step includes detecting a repetitive non-reentrant ventriculo-atrial synchronous rhythm when the cardiac rate is above a given rate and failing to detect an atrial evoked response.

38. The method of claim 31 wherein the step of providing therapy includes the step of resetting the AV delay following the secondary pacing pulse.

39. The method of claim 31 wherein the step of providing therapy includes the step of causing the pulse generator to deliver a tertiary atrial pacing pulse following the secondary pulse.

40. The method of claim 39 wherein the step of providing therapy includes the step of causing the pulse generator to deliver the tertiary atrial pacing pulse after a ventricular even following the secondary atrial pacing pulse.

41. The method of claim 39 wherein the step of providing therapy includes providing the tertiary atrial pacing pulse about 200 to 350 milliseconds after the secondary atrial pacing pulse.

42. The method of claim 39 further including the step of detecting cardiac rate and wherein the step of providing therapy includes causing the pulse generator to terminate deliver of the tertiary atrial pacing pulses when the cardiac rate is below a predetermined rate.

43. The method of claim 39 further including the step of determining an atrio-ventricular complex type for each cardiac cycle of the heart including an AR complex wherein an atrial pacing pulse is followed by an R wave and a PR complex wherein an intrinsic atrial event is followed by an R wave and wherein the step of providing therapy includes causing the pulse generator to terminate delivery of the tertiary atrial pacing pulses responsive to an AR complex or a PR complex.

44. The method of claim 31 wherein the step of providing therapy includes the step of causing the pulse generator to deliver the secondary atrial pacing pulse after a ventricular event following the primary atrial pacing pulse.

45. The method of claim 31 wherein the step of providing therapy includes the step of causing the pulse generator to deliver the secondary atrial pacing pulse about 200 to 350 milliseconds after the primary atrial pacing pulse.

46. The method of claim 44 wherein the step of providing therapy includes terminating deliverance of the secondary atrial pacing pulse after a predetermined number of cardiac cycles.

* * * * *